United States Patent [19]
Jenkins et al.

[11] Patent Number: 5,770,800
[45] Date of Patent: Jun. 23, 1998

[54] FLEXIBLE ULTRASONIC PIPE INSPECTION APPARATUS

[75] Inventors: Charles F. Jenkins, Aiken, S.C.; Boyd D. Howard, Augusta, Ga.

[73] Assignee: The United States of America as represented by the United States Department of Energy, Washington, D.C.

[21] Appl. No.: 659,598

[22] Filed: Aug. 6, 1996

Related U.S. Application Data

[63] Continuation of Ser. No. 312,644, Sep. 27, 1994, abandoned.

[51] Int. Cl.[6] ................................................ G01N 29/24
[52] U.S. Cl. ........................ 73/623; 73/865.8; 73/866.5; 348/84
[58] Field of Search ..................... 73/623, 151, 40.5 A, 73/49.1, 49.5, 865.8, 866.5; 254/134.5; 324/220; 376/849; 348/84.85

[56] References Cited

U.S. PATENT DOCUMENTS

| | | | |
|---|---|---|---|
| 3,817,089 | 6/1974 | Eggleton et al. | 73/623 |
| 3,938,502 | 2/1976 | Bom | 73/636 |
| 4,241,609 | 12/1980 | Bergman et al. | 73/623 |
| 4,372,161 | 2/1983 | de Buda et al. | 73/623 |
| 4,460,920 | 7/1984 | Weber et al. | 73/623 |
| 4,572,201 | 2/1986 | Kondo et al. | 73/623 |
| 4,607,925 | 8/1986 | Kamigaichi | 348/84 |
| 4,757,821 | 7/1988 | Snyder | 73/623 |
| 4,834,102 | 5/1989 | Schwarzchild et al. | 73/623 |
| 4,920,804 | 5/1990 | Iwamoto et al. | 73/623 |
| 4,955,235 | 9/1990 | Metala | 73/623 |
| 5,090,259 | 2/1992 | Shishido et al. | 73/866.5 |
| 5,313,838 | 5/1994 | Gondard | 73/623 |
| 5,398,560 | 3/1995 | Zollinger | 73/623 |

*Primary Examiner*—Christine K. Oda
*Attorney, Agent, or Firm*—Harold M. Dixon; William R. Moser; Paul A. Gottlieb

[57] ABSTRACT

A flexible, modular ultrasonic pipe inspection apparatus, comprising a flexible, hollow shaft that carries a plurality of modules, including at least one rotatable ultrasonic transducer, a motor/gear unit, and a position/signal encoder. The modules are connected by flexible knuckle joints that allow each module of the apparatus to change its relative orientation with respect to a neighboring module, while the shaft protects electrical wiring from kinking or buckling while the apparatus moves around a tight corner. The apparatus is moved through a pipe by any suitable means, including a tether or drawstring attached to the nose or tail, differential hydraulic pressure, or a pipe pig. The rotational speed of the ultrasonic transducer and the forward velocity of the apparatus are coordinated so that the beam sweeps out the entire interior surface of the pipe, enabling the operator to accurately assess the condition of the pipe wall and determine whether or not leak-prone corrosion damage is present.

19 Claims, 2 Drawing Sheets

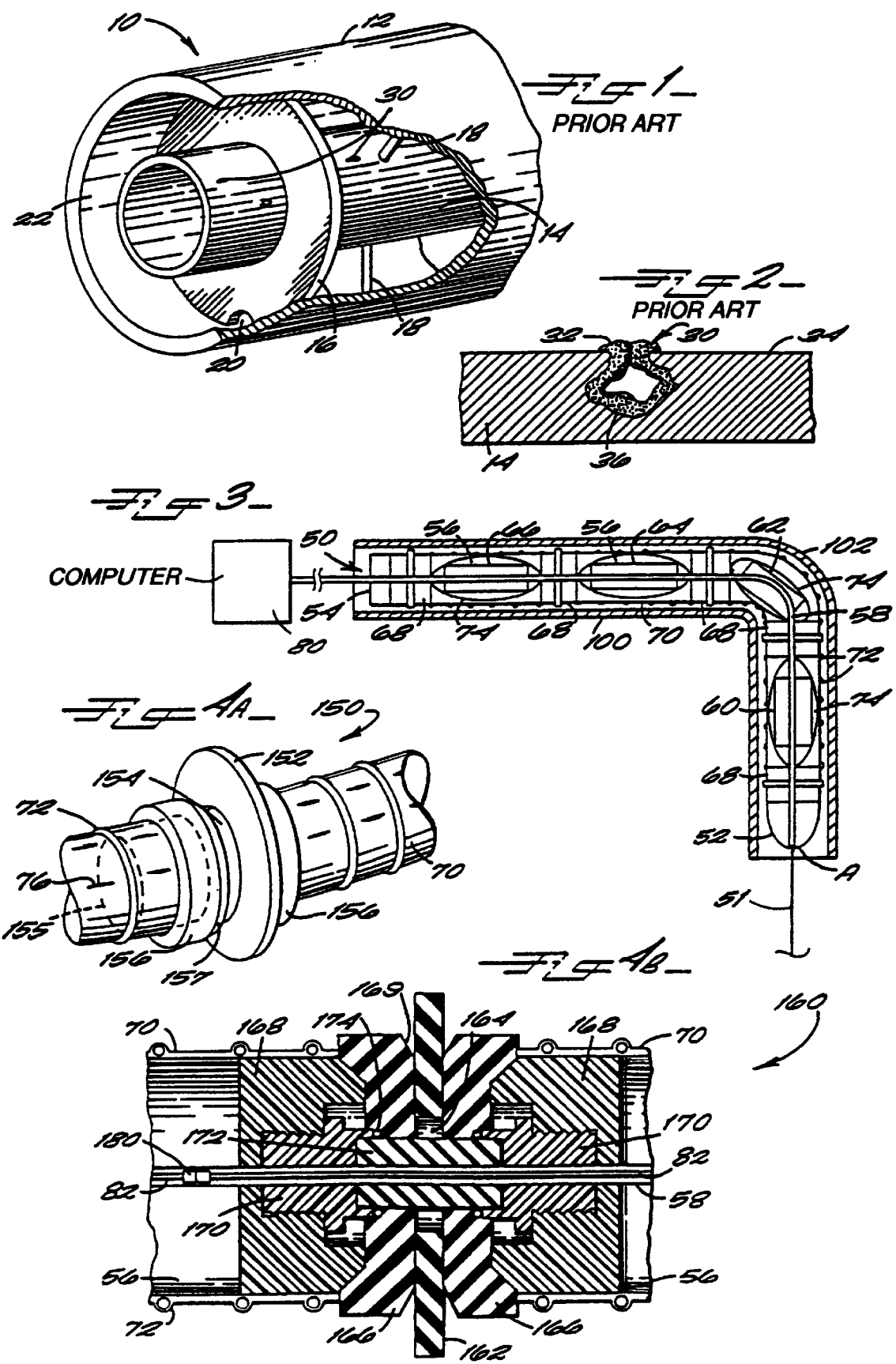

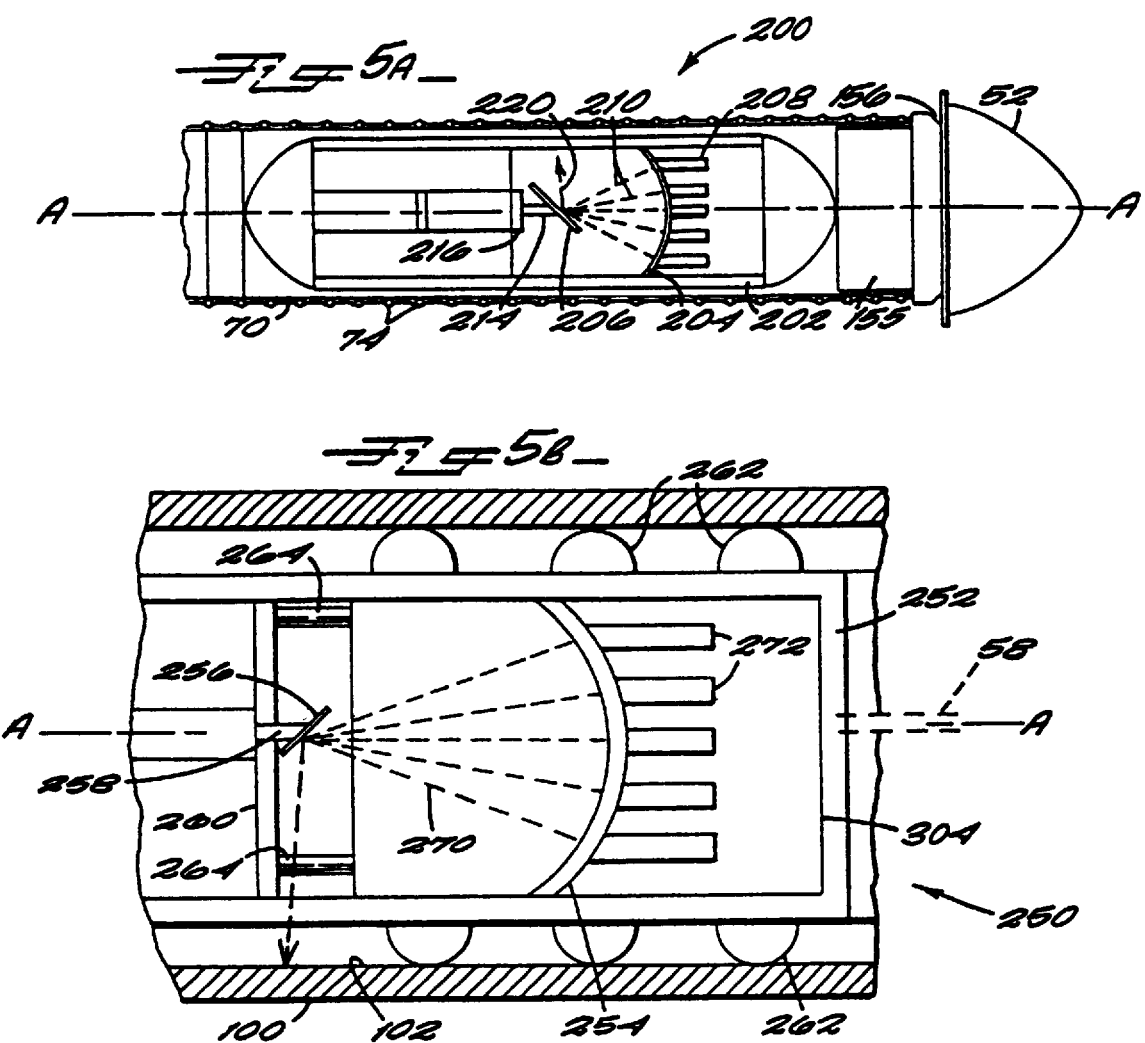

FLEXIBLE ULTRASONIC PIPE INSPECTION APPARATUS

This application is a continuation, of application Ser. No. 08/312,644 filed Sep. 27, 1994, now abandoned.

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to pipe inspection apparatus. In particular, the present invention relates to a modular ultrasonic pipe inspection apparatus that flexes to negotiate severe bends in small diameter piping systems.

2. Discussion of Background

Pipe crawlers, pipe inspection "rabbits" and similar vehicles are widely used for inspecting the interior surfaces of piping systems, storage tanks and process vessels for damaged or flawed structural features. Typically, such devices include a testing probe, such as an ultrasonic probe or eddy current probe, carried by a support structure that travels through the piping system being inspected.

A number of U.S. patents disclose ultrasonic testing probes, including endoscopic probes for use in medical procedures, and probes and pipe crawlers for moving through and inspecting piping systems. Several devices have ultrasonic transducers that are rotatably controlled by a motor or a motor-driven shaft (Schwarzchild, et al., U.S. Pat. No. 4,834,102; Kondo, et al., U.S. Pat. No. 4,572,201; Bom, U.S. Pat. No. 3,938,502; Eggleton, et al., U.S. Pat. No. 3,817,089). Schwarzchild, et al. provide a position sensing means for determining the exact angular orientation of the ultrasonic transducer.

A variety of pipe inspection devices are available. Weber, et al. (U.S. Pat. No. 4,460,920) describes a remote-controlled pipe crawler having front and rear stepping bodies joined by a gimbal joint. Shishido, et al. (U.S. Pat. No. 5,090,259) and DeBuda, et al. (U.S. Pat. No. 4,372,161) disclose pneumatically-controlled pipe crawlers that are capable of negotiating bends in piping. A flexible shaft carrying a rotatable support for an ultrasonic transducer is shown by Bergman, et al. (U.S. Pat. No. 4,241,609). Iwamoto, et al. (U.S. Pat. No. 4,920,804) discloses an ultrasonic probe with a flexible shaft connected to an axially-aligned rotatable ultrasonic transducer section. The probe includes means for centering the transducer with respect to the piping being inspected.

The need for highly flexible inspection apparatus is especially evident in piping systems wherein an outer pipe contains one or more smaller-diameter pipes that are used to transport fluids. As seen in FIG. 1, such a piping system 10 may include an outer pipe 12 that surrounds an inner pipe 14, serving as a containment for the contents of pipe 14 in case of leakage. Pipe 14 is supported in position by a series of disks 16 or spokes 18. Disk 16, if present, may have a vent 20 formed therethrough to allow circulation of fluids through an annular volume 22 between pipes 12 and 14, preventing accumulation of gases or liquids in any single portion of volume 22. Pipe 12 may be provided with vents or drain holes (not shown) for draining fluids that accumulate in volume 22. Leak detectors may be positioned inside or outside pipe 12.

Piping systems such as system 10 must be inspected periodically in order to provide assurance of their structural integrity and detect the presence of corrosion, damaged welds or seams, etc. before the occurrence of detectable leaks. If pipe 14 is used to transport hazardous fluids, it is important to detect and repair damage before leakage occurs. By the time leakage from pipes 12 and 14 is evident, there may be relatively major structural damage to system 10.

Pipe 14 may corrode from the inside out due to the corrosive action of the contents. In addition, pipes 12 and 14 may corrode by a mechanism known as microbiologically-induced corrosion (MIC) that can cause structural defects such as pits 30 (FIGS. 1, 2). Microbiologically-induced corrosion is caused by colonies of bacteria 32 that settle on an outer or inner surface 34 of pipe 12 or 14. Bacteria 32 derive nourishment from the environment within volume 22 or inside pipe 14, which may contain gases, water and other liquids, etc., depending on the environment of piping system 10 and the materials transported therein. As bacteria 32 grow and multiply, they produce highly acidic, corrosive wastes that corrode the material of pipe 14. A characteristic of MIC is that, as the wastes produced by bacteria 32 corrode pipe 14, a bacteria-lined void space 36 is formed. Void 36 may eventually enlarge sufficiently to penetrate through the pipe wall, leading to leakage of the contents of the pipe. Detection of voids and other structural defects induced by MIC—indeed, of defects induced by any destructive causes—is essential for the safe, efficient conduct of operations involving radioactive and other hazardous materials.

Visual inspection is a traditional method for detecting structural defects or leaks in piping systems, and is feasible when the pipes are above-ground and/or easily accessible. However, visual inspection is inadequate for piping systems that are not easily accessible, for annular piping systems having a concealed inner pipe, or when dealing with minute structural defects. Damage to inner pipe 14 cannot be easily detected from outside the pipe: outer pipe 12 masks eddy current or ultrasonic signals from inner pipe 14 when the testing device is outside pipe 12, and pipe supports 16, 18 interfere with the movement of pipe crawlers, boroscopes and other inspection devices in volume 22.

There is a need for a pipe inspection apparatus that can detect structural flaws in annular piping systems. The apparatus should be dimensioned to pass through various sizes of piping, and be able to readily negotiate bends in the piping. In addition, it should be capable of providing continuous location and mapping capabilities so that any detected flaws can be located and repaired.

SUMMARY OF THE INVENTION

According to its major aspects and broadly stated, the present invention is a flexible, modular ultrasonic pipe inspection apparatus. The apparatus has a plurality of modules carried by a flexible shaft, including a nose section, a tail section, at least one rotatable ultrasonic transducer, a motor/gear unit, and a position/signal encoder. The modules are connected by flexible joints that enable the apparatus to negotiate bends in piping by allowing each module to change its relative orientation with respect to the neighboring modules. The motor unit rotates the transducer about the longitudinal axis of the apparatus for scanning the inner surface of a pipe.

An important feature of the present invention is the transducer. The apparatus includes one or more rotatable ultrasonic transducers, preferably arranged to sweep across a 360° arc. The rotational speed of the transducer about its longitudinal axis and the forward velocity of the apparatus along the axis may be coordinated so that the ultrasonic beam sweeps out all or most of the interior surface of the pipe as the apparatus navigates therethrough, enabling the operator to accurately assess the condition of the pipe wall and determine the location of leak-prone corrosion damage by analyzing the reflected beam.

The flexible joints constitute another important feature of the present invention. The joints flex freely to allow each module of the apparatus to change its relative orientation with respect to a neighboring module as the apparatus moves around a tight corner in a piping system. The joints may be knuckle joints, gimbal joints, universal joints, molded silicon joints or the like that provide sufficient flexibility to pass over weld crowns and other protrusions inside a pipe.

Another feature of the present invention is the flexible shaft. The shaft passes through the modules and the joints, and is made of a flexible, resilient material such as polyvinyl chloride (PVC), polytetrafluoroethylene, or silicone rubber tubing that flexes to help the apparatus negotiate bends and obstructions in the piping being inspected. The shaft also provides a channel for electrical cables that connect the individual modules of the apparatus. For example, the shaft may carry electrical wiring forward from the motor/gear unit and the position/signal encoder unit to the ultrasonic transducer and back.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a cut-away view of an annular piping system;

FIG. 2 is a longitudinal cross-sectional view of a pipe wall of the piping system of FIG. 1, showing a corrosion pit;

FIG. 3 is a schematic, cross-sectional view of a pipe inspection apparatus according to a preferred embodiment of the present invention, deployed in a pipe;

FIG. 4A is an exterior view of a flexible joint according to one preferred embodiment of the present apparatus of FIG. 3;

FIG. 4B is another preferred embodiment of a flexible joint for use in the apparatus of FIG. 3;

FIG. 5A is a preferred embodiment of a rotatable ultrasonic transducer for use in the apparatus of FIG. 3; and FIG. 5B is another preferred embodiment of a rotatable ultrasonic transducer for use in the apparatus of FIG. 3.

DETAILED DESCRIPTION OF A PREFERRED EMBODIMENT

In the following description, like reference numerals refer to and identify the same structures, areas or surfaces as they are used in the different figures.

Referring now to FIG. 3, there is shown a pipe inspection apparatus 50 according to a preferred embodiment of the present invention. Apparatus 50 includes a flexible, modular body having a head or nose module 52, a tail module 54, and a plurality of modules 56 carried by a flexible, hollow shaft 58. Modules 56 may include components such as a transducer 60 (preferably an ultrasonic transducer), a motor/drive unit 62 connected to transducer 60 by a flexible driveshaft, a position/signal encoder 64, and an electronics package 66 for processing information received from transducer 60. Additional modules 56, if present, may include eddy current detection devices, video cameras, radiation level probes or other types of measuring instruments, and a self-contained power supply for operating various modules 56. Alternatively, apparatus 50 may be connected to an external power source. Modules 56 are connected to each other and to nose 52 and tail 54 by flexible joints 68.

The components of apparatus 50 may be in separate modules 56 as shown in FIG. 3, or a single module 56 may contain two or more components. For example, transducer 60 and motor unit 62 may be contained in a single module 56, or transducer 60, motor unit 62 and encoder 64 may be in the same module. Shaft 58 is preferably hollow, and may contain cable for electrically connecting modules 56 to each other.

Nose 52 and tail 54 are preferably made of a compressible, resilient material such as silicone rubber that allows nose 52 and tail 54 to deform as needed to negotiate bends 102 and obstructions in a pipe 100. Nose 52 and tail 54 may be tapered generally as shown in FIG. 3; alternatively, nose 52 and tail 54 may be similarly shaped for ease in navigating pipe 100 in either direction. Apparatus 50 has an outer casing 70 made of a flexible, resilient, moisture-resistant, low-friction material such as polyvinyl chloride (PVC), polytetrafluoroethylene (TEFLON®), urethane, or tear-resistant, flexible silicone rubber. Casing 70 may be formed of corrugated tubing that carries a plurality of ribs 72 that help apparatus 50 negotiate bends 102. Ribs 72 may be in the form of a coil or rings attached to casing 70, or be integrally formed with casing 70. Casing 70 helps prevent apparatus 50 from becoming lodged within pipe 100 on weld crowns or other obstacles within the pipe. Modules 56 may be enclosed in suitable lengths of PVC piping, or molded into bodies 74 of silicone rubber, electrical resin encapsulant or other suitable material. Casing 70 may be applied by shrink-wrapping the casing material onto modules 56. As used herein, the term "shrink wrapping" means any process that causes a thin layer of a material to conform to the outside contours of a body. Typically, a sleeve of such a material is fitted over the underlying body. Upon the application of heat, the material shrinks and conforms closely to the contours of the body. In order to increase flexibility while maintaining the slipperiness of apparatus 50, casing 70 can be provided with radial slits 76 (FIG. 4A).

Shaft 58 passes through the centers of modules 56 and joints 68, helping maintain the modules and joints in axial serial relationship. Modules 56 may be electrically connected to each other and to a remotely-located computer/controller 80 by a cable or cables 82 carried in the hollow interior of shaft 58 (shown in FIG. 4B). Shaft 58 encloses cables 82, preventing the cables from kinking, breaking, binding, or becoming lodged on obstacles within the interior of pipe 100 as apparatus 50 moves through the pipe. Shaft 58 may be in the form of a single length of hollow tubing that carries some or all of modules 56 and joints 68. Alternatively, shaft 58 may consist of sections of tubing that connect adjacent modules 56 to each other.

Apparatus 50 is used to inspect pipe 100, which may have an internal diameter as small as approximately ½" (about 1.3 cm), one or more severe bends 102 and an axis A (FIG. 3). The inner surface of pipe 100 may have obstructions such as weld crowns (not shown) that protrude into the interior of the pipe. Apparatus 50 is moved through pipe 100 by any suitable means, for example, a flexible tether or drawstring 51 attached to nose 52 or tail 54, by differential hydraulic pressure, or by attaching apparatus 50 to a pipe pig (a device that fits snugly inside a pipeline and can be sent through it). When deployed in pipe 100, the longitudinal axes of modules 56 and joints 68 approximately coincide with axis A.

Flexible joints 68 may be any type of joint that provides a pass-through for shaft 58 and cable 82 and, when connecting a module 56 to nose module 52 or tail module 54, or connecting two adjacent modules 56 to each other, flexes to allow each module to change its relative orientation with respect to a neighboring module. Joints 68 may be knuckle joints that pivot in any angular direction with respect to a central axis, gimbal joints having two mutually perpendicular and intersecting axes of rotation for free angular movement in two directions, or universal joints, linkages that transmit rotation between two shafts whose axes are coplanar but not necessarily coinciding.

Preferably, flexible joints 68 are the type of flexible knuckle joint described in commonly-assigned patent application Ser. No. 08/089,679, filed Jul. 12,1993 (Apparatus For Inspecting Piping) now U.S Pat. No. 5,398,560, the disclosure of which is incorporated herein by reference. A joint 150 includes a flat, flexible annular seal 152 made of polyurethane, silicone rubber or similar material, with a center hole 154 (FIG. 4A). Seal 152 is connected to adjacent modules 56 by molding silicone rubber portions 156 onto the ends of modules 56, covered by coating 70, and through hole 154. Each portion 156 is pivotable with respect to the other portion 156, in any angular direction about hole 154. When either portion 156 pivots with respect to the other, portions 156 do not pull through hole 154, but pull away from seal 152 as joint 150 flexes. Thus, joint 150 flexes to allow neighboring modules 56 to change their relative orientation with respect to each other.

Portions 156 fit snugly onto casing 70, and are preferably bonded or cemented to casing 70 to ensure that moisture does not penetrate into the interior of apparatus 50. If casing 70 and portions 156 are made of materials that cannot readily be bonded to one another, portions 156 may include a flexible inner sleeve 155, made of a material that can be permanently attached to the material of casing 70, by bonding, cementing, gluing and so forth. By way of example, if portions 156 are silicone rubber and casing 70 is made of PVC tubing, sleeve 155 is PVC tubing or a similar material that can be bonded to casing 70.

Preferably, portions 156 are shaped so that the outer diameter of each portion 156 proximal to seal 152 is smaller than the diameter distal to the seal. Portions 156 may be tapered towards seal 152, or have annular notches 157 as shown in FIG. 4A. Notches 157 accommodate the flexing of seal 152 when the seal passes an obstruction in pipe 100, facilitating movement of apparatus 50 through the pipe. Seals 152 preferably have an outer diameter approximately equal to the internal diameter of pipe 100, thus, seals 152 serve to center apparatus 50 (and modules 56) within the pipe. Apparatus 50 may be adapted for inspecting piping of different internal diameters simply by varying the diameter of seals 152. The optimum configuration of joint 150, including the dimensions of portions 156, notches 157, and seal 152, is best determined in view of the dimensions of the piping system to be inspected and the size of modules 56.

Another type of flexible knuckle joint usable with the invention is shown in FIG. 4B. A joint 160 includes an annular seal 162, similar to seal 152 of joint 150, with silicone rubber portions 166 molded through a hole 164. Alternatively, portions 166 may be integrally formed with seal 162. Portions 166 engage adapters 168, which are molded onto the ends of modules 56. A male tubing quick-connect 170 is threaded into each adapter 168. A section 172 of flexible tubing is attached to quick-connects 170 by collets 174. Coating 70 is attached to adapters 168, by bonding, cementing or other suitable means. Seal 162, portions 166, adapters 168 and tubing 172 are made of flexible, resilient materials such as silicone rubber, PVC, polyurethane and so forth.

When section 172 is attached to both quick-connects 170, portions 166 engage adapters 168, which in turn engage their respective modules 56. Thus, section 172 holds adjacent modules 56 together and provides a pass-through for flexible shaft 58 and cable 82. Section 172 flexes so that each portion 166 is pivotable at center hole 164 with respect to the other portion 166 in any angular direction, allowing neighboring modules 56 to change their relative orientation with respect to each other when joint 160 flexes. Portions 166 have annular notches 169 to accommodate the flexing of seal 162 when passing an obstruction in pipe 100.

Section 172 may be released from quick-connects 170 by depressing collets 174. A connector 180 allows disconnecting shaft 58 and cable 82 when adjacent modules 56 are separated. Use of one or more detachable joints 160 allows the corresponding modules 56 to be readily separated from each other, for example, for inspection and routine maintenance, to replace a defective module 56, and so forth.

Apparatus 50 preferably includes at least one flexible joint 68, preferably a joint such as above-described knuckle joints 150, 160 or some other type of joint that allows flexing of adjacent modules 56 with respect to each other. Preferably, joints 68 connect nose 52 and tail 54 to the immediately-adjacent modules 56, and adjacent modules 56 to one another. Joints 68 and shaft 58 flex as corresponding modules 56 passes through bends in a piping system; electrical wiring 82 (if present) is protected by shaft 58. When joints 68 are the type of knuckle joint shown in FIGS. 4A and 4B, portions 156, 166 pull away from seals 152, 162, respectively, allowing apparatus 50 to flex easily at the respective seal locations. Seals 152, 162 also deform by folding back as apparatus 50 passes weld crowns and other obstacles inside a pipe.

Electronics package 66, if present, receives and processes data from transducers 60, and transmits the data to computer 80 via cable 82. Package 66 may contain one or more circuit boards embedded in a nonconductive buffer material, which is then encapsulated in silicone rubber, electrical resin, or other suitable material to form a module 56. Apparatus 50 may include a plurality of such packages 66. Alternatively, the requisite electronics may be packaged together with transducer 60 or other components of apparatus 50, or the data may be sent directly to computer 80 for on-line, real time analysis. If desired, package 66 may store data from transducer 60 for later, off-line analysis.

Cable 82 passes through flexible shaft 58 to electrically connect modules 56, and may also connect apparatus 50 to computer 80. If desired, a portion of cable 82 may be wound on a removable spool contained within one of modules 56, preferably near tail 54, that holds a predetermined amount of communication wire, as described in the above-referenced patent application. Cable 82, which may be as long as 900'(about 275 m), is played out of tail 54 as apparatus 50 travels through pipe 100. Other methods of communication between apparatus 50 and computer 80 can be used with the invention, including fiber optic cables, RF broadcasting using pipe 100 as an antenna, and storage of data in an on-board memory for later processing.

In a preferred embodiment of the present invention, apparatus 50 includes at least one phased-array, focused, ultrasonic transducer such as a transducer 200 shown in FIG. 5A. In this type of transducer, also called a focused-array ultrasonic transducer, a plurality of concentric, circular transmitting/receiving elements are pulsed separately to generate a very high intensity ultrasonic beam focused at a portion of the pipe. The reflected beam is received by transducer 60 and analyzed by means well known in the art to determine the condition of that portion of the pipe, including the presence (or absence) of structural defects, voids, and so forth. Variable phasing of the elements ensures that control of the focal point location within the component being tested may be accomplished over a wide range of depths. The directed, focused ultrasonic beam is coupled in water, liquid silicone, or other suitable liquid medium to the component being tested. For contact-type ultrasonic inspection, the coupling fluid may be contained within a specially designed fluid-filled wedge that has a tough flexible membrane through which the ultrasonic beam passes into the component.

Transducer 200 includes a multiple-element, phased array, focused ultrasonic transducer 202 with a focusing lens 204, and a rotatable reflector 206. Transducer 200 constitutes a large-aperture, broadband, multi-element search unit, with a plurality of concentric, circular elements 208. Three concentric elements 208 are shown, however, it will be understood that a different number of elements 208 may be used. Each element 208 generates an ultrasound beam 210 that is focused onto reflector 206 by lens 204. Elements 208 are used to produce a small, circular spot with each element pulsed separately to generate a high intensity ultrasonic beam. Reflector 206 is carried by a shaft 214, rotatably mounted to a base 216. Transducer 200 may include a motor for rotating shaft 214; alternatively, shaft 214 may be rotated by a motor unit 62 as described above.

Combined beam 220 is reflected towards the inner surface of pipe 100, in a direction approximately transverse to the longitudinal axes of transducer 200 and pipe 100 (axis A in FIG. 5A). As reflector 206 rotates, beam 220 sweeps across the inner surface of pipe 100 and is reflected by the pipe, describing an approximately helical path across the surface as apparatus 50 moves axially through the pipe. Transducer 200 generates a signal in response to reflected beam 220 and transmits the signal to electronics package 66 (if present) via cable 82, then to computer 80 where the signal is analyzed to determine the condition of pipe 100.

Alternatively, apparatus 50 may include an ultrasonic transducer 250 as shown in FIG. 5B. Transducer 250, like transducer 200, is a multiple-element, phased-array, focused, ultrasonic transducer with a body 252, a focusing lens 254, a rotatable reflector 256, a shaft 258 rotatably mounted to a base 260, and centering devices 262. Centering devices 262 maintain transducer 250 centered within pipe 100. Devices 262 may be positioned generally as shown, or take the form of a module or modules 56. Base 260 is spaced apart from body 252, and attached to body 252 by a plurality of rods 264, preferably at least three rods. As reflector 256 rotates, a focused ultrasonic beam 270 from elements 272 sweeps across the inner surface of pipe 100, approximately transverse to longitudinal axis A, describing an approximately helical path across the surface as device 50 moves axially in the pipe.

Apparatus 50 includes at least one rotatable ultrasonic transducer, preferably a transducer with reflectors such as 206, 256 rotatable in such a manner that a 360-degree arc is scanned. That is, if apparatus 50 has a single ultrasonic transducer, the transducer is rotatable through 360 degrees. If apparatus 50 has two transducers, preferably separated by a flexible joint 68, each transducer is rotatable through an arc of at least 180 degrees. Similarly, if apparatus 50 has three transducers, each transducer is rotatable through an arc of at least 120 degrees so that the full 360-degree arc is scanned.

In use, cable 82 is connected to computer 80 and apparatus 50 is deployed in pipe 100. Apparatus 50 is moved through pipe 100, controlled by computer 80, to inspect the walls of the pipe for flaws. When apparatus 50 is in operation, transducer 60 transmits an ultrasonic beam towards a portion of the wall of pipe 100, preferably in a direction approximately transverse to the direction of movement of apparatus 50 (i.e., transverse to longitudinal axis A). If desired, the focus of the transmitted ultrasonic beam may be varied to scan the thickness of the pipe wall. The reflected beam contains information relating to the structure of that portion of pipe 100. An electrical signal corresponding to the reflected beam is sent from transducer 60 to electronics package 66 (if present), and sent back to computer 80 via cable 82. This data is correlated with signals corresponding to the axial position of apparatus 50 in pipe 100 and the angular position of transducer 60. The condition of pipe 100 is determined by analyzing the data to determine the size, configuration and location of flaws or structural defects (if any) within the pipe wall. Preferably, computer 80 generates a real-time display that allows the operator to map the locations of any detected flaws.

The rotating ultrasonic beam transmitted by transducer 60 sweeps out a helical path as apparatus 50 moves axially through pipe 100. Transducer 60 is rotated by motor unit 62, or, if transducer 60 is the type of ultrasonic transducer shown in FIGS. 5A and 5B, reflectors 206 or 256 are rotated by motor unit 62 to scan pipe 100. Preferably, computer 80 controls the movement of apparatus 50 and the beam focus to ensure that substantially all of the volume of the pipe wall is inspected. Computer 80 may control the rotational speed of transducer 60, the axial velocity of apparatus 50, or both, to coordinate rotation of transducer 60 with the axial movement of apparatus 50 to ensure that an ultrasonic beam from the transducer sweeps out all or most of the inner surface of pipe 100. Alternatively, a preselected sample of the pipe wall is inspected, and standard statistical analysis techniques are used to determine whether or not the entire wall is substantially free of defects.

Integrating a rotating focused array transducer with a highly flexible delivery device such as apparatus 50 provides the capability for inspecting piping systems that may not be readily accessible from the outside. The modular construction of apparatus 50, with individual modules carried by a flexible shaft 58 and connected by flexible joints 68, enables the apparatus to negotiate small-diameter pipe bends by allowing each module to bend and flex with respect to the other modules. Transducers such as above-described transducers 200, 250 are capable of being electronically focused at variable depths within the volume of the pipe wall being tested. If desired, transducers 200, 250 may be provided with electronics for processing data and water-filled wedge couplers for contact-type ultrasonic testing. In addition, transducers 200, 250 may be provided with a set of interchangeable lenses 204, 254, respectively, having different focal lengths to compensate for different diameters of the pipe being inspected. Apparatus 50 is capable of being remotely controlled, and providing ultrasonic images in real-time.

It will be apparent to those skilled in the art that many changes and substitutions can be made to the preferred embodiment herein described without departing from the spirit and scope of the present invention as defined by the appended claims.

What is claimed is:

1. An apparatus for inspecting piping, said apparatus comprising:

a body having an axis, said body made of a resilient material;

an inspection instrument carried by said body comprising an ultrasonic transducer having a plurality of transmitting elements for generating a focused single high intensity ultrasonic beam, said beam being directed by a positionable reflector for directing the focused beam across the inner-surface of a pipe in a helical path as said apparatus moves axially through said pipe;

a flexible outer-surface comprising a flexible tube having a plurality of ribs formed thereon for increasing the flexibility of said body transverse to said axis so that said apparatus can pass through bends in said piping, said flexible outer surface covering said body and said ultrasonic transducer;

means for connecting a plurality of consecutive modules comprising said body to one another flexibly so that said connecting means flexes to allow said modules to change a relative orientation thereof.

2. The apparatus according to claim 1 wherein said apparatus further comprises a means for moving said plurality of consecutive modules through said pipe.

3. The apparatus according to claim 2 wherein said apparatus further comprises a means for rotating said inspection instrument about said axis.

4. The apparatus according to claim 3 wherein a controlling means controls said moving means and said rotating means so that a plurality of inspection instruments direct a respective ultrasonic beam at a helical series of a portion of a wall of said inner surface of said pipe, each said portion of said wall having a combined area corresponding to a preselected fraction of said pipe wall.

5. The apparatus according to claim 4 wherein said controlling means further comprises means for coordinating rotation of said apparatus and axial movement of said apparatus so that said fraction is approximately unity.

6. A sensing apparatus for use with a pipe crawler transport, said apparatus comprising:

a hollow housing suitable for insertion within an interior chamber of a pipe crawler;

an ultrasonic transducer carried within said housing, comprising a plurality of elements for the production of a plurality of ultrasonic beams along multiple pathways;

a focusing element having a first side adjacent to said plurality of elements, said focusing element positioned along said pathways, the focusing element receiving the plurality of beams and converging the plurality of beams into a single high intensity ultrasonic beam along a single beam pathway; and a positionable reflector opposite a second side of said focusing element and within said single beam pathway, said reflector adapted for varying a direction of a reflected pathway of said high intensity ultrasonic beam.

7. The apparatus of claim 6, wherein the ultrasonic transducer further comprises a plurality of elements in a phased array, producing a plurality of ultrasonic beams.

8. The apparatus of claim 6, wherein the plurality of elements produces a plurality of pulsed ultrasonic beams.

9. The apparatus of claim 6, wherein the focusing element focuses the plurality of ultrasonic beams onto the positionable reflector.

10. The apparatus of claim 6, wherein the positionable reflector further comprises a shaft that the reflector is mounted on, the shaft is movable over a 360 degrees arc.

11. The apparatus of claim 6, wherein the plurality of elements further comprises a receiving element for receipt of the ultrasonic beam reflected by the pipe wall.

12. The apparatus of claim 11, wherein the receiving element further comprises an electrical package that generates an electrical signal in relation to the ultrasonic beam received.

13. An apparatus for inspecting a wall of a pipe, said apparatus comprising:

a hollow housing suitable for insertion within an interior chamber of a pipe crawler transport;

an ultrasonic transducer carried within said housing comprising:

a plurality of elements for the production of a plurality of ultrasonic beams along a plurality of pathways;

a focusing element positioned within the pathways of the beams, the focusing element converging the plurality of beams into a single high-intensity beam;

a positionable reflector opposite the focusing element from the plurality of elements, and within the pathway of the high-intensity beam;

wherein the ultrasonic transducer generates the plurality of ultrasonic beams, the beams are focused by the focusing lens, forming the single high-intensity beam, the beam directed by the positionable reflector to the inner-surface of a pipe as the pipe crawler transport moves axially through the pipe.

14. The apparatus of claim 13, wherein the plurality of elements further comprise the generation of the plurality of beams by a pulsed operation of the plurality of elements.

15. The apparatus of claim 13, wherein the focusing element focuses the single high-intensity ultrasonic beam onto the positionable reflector.

16. The apparatus of claim 13, wherein the positionable reflector further comprises a rotatable shaft onto which the reflector is mounted, the shaft is rotatable over a 360 degrees arc.

17. The apparatus of claim 13, wherein the plurality of elements receive the ultrasonic beam reflected by the pipe wall, after reflection by the positionable reflector.

18. The apparatus of claim 17, wherein the plurality of elements further comprise an electrical circuit that generates a plurality of electrical signals, each signal having an intensity in direct relation to the intensity of each reflected ultrasonic beam received.

19. The apparatus of claim 18, wherein the plurality of electrical signals are transmitted to a computer for analysis.

* * * * *